Feb. 25, 1941. J. GAUJARD Plant Pat. 453
ROSE PLANT
Filed Oct. 14, 1940
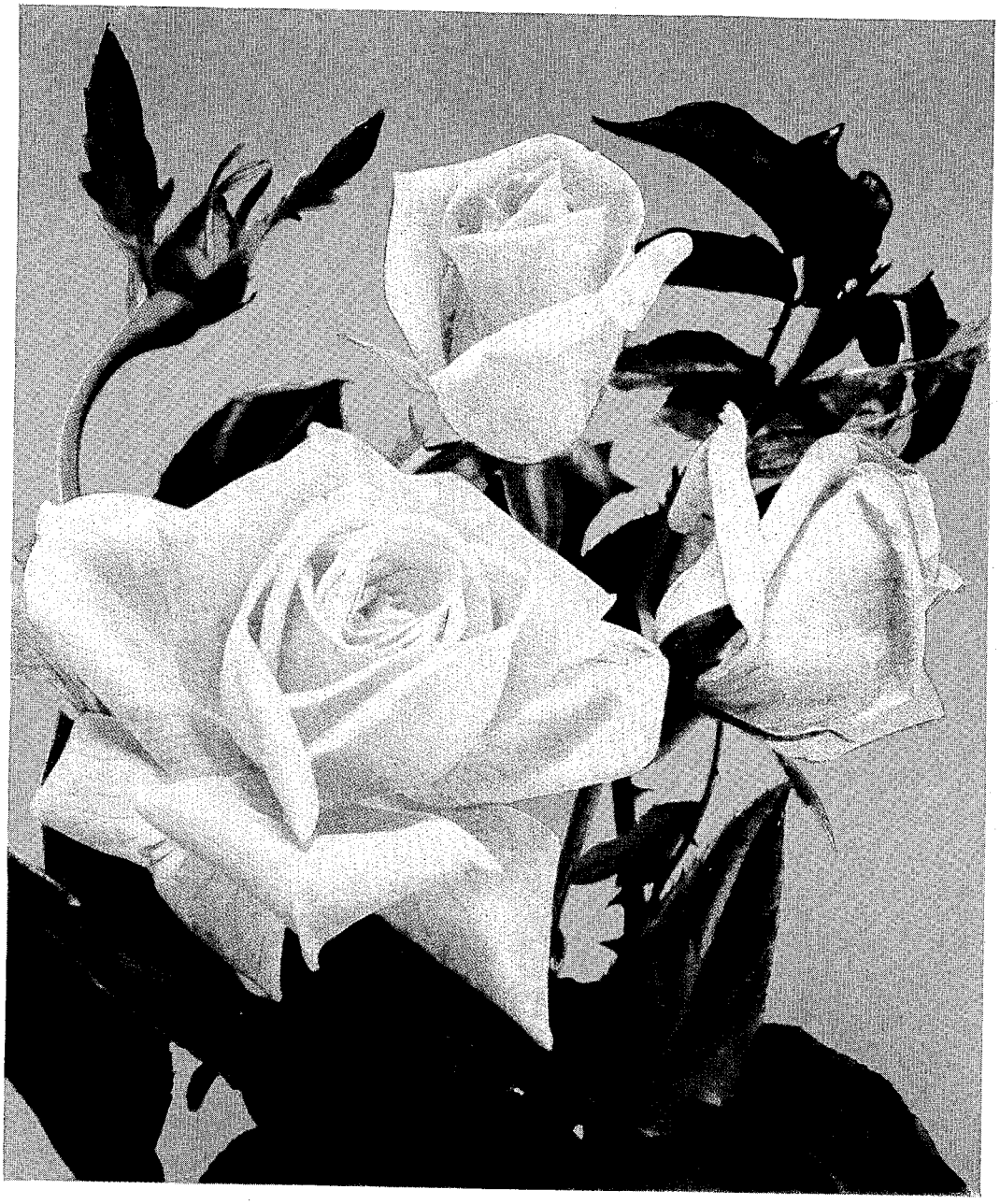
Inventor
J. Gaujard
By Robb & Robb
Attorneys Patented Feb. 25, 1941

UNITED STATES PATENT OFFICE

453

ROSE PLANT

Jean Gaujard, Feyzin, France, assignor to Jackson & Perkins & Company, Newark, N. Y.

Application October 14, 1940, Serial No. 361,193

1 Claim. (Cl. 47—61)

This invention relates to a new and distinct variety of hybrid tea rose, marked primarily for the gracefulness of its flowers and their informal appearance when open.

The new rose is noted for its vigorous branching habit and freedom of flowering, but more particularly an important feature of novelty resides in the peculiar formation of the sepals which are branched and almost large enough to be termed miniature leaves.

Other distinguishing characteristics found in this new variety are, the very small calyx which contains only a small number of ovaries, the majority of which protrude inside the flower, and the luminous Rose Doree color of the flowers which fades to Eosine Pink in the final stages.

This new rose has been asexually reproduced and found to come true to form.

The following is a detail description of the new variety, the color designations being in accord with Ridgway's Color Standard.

Parentage:

*Seed parent.*—Mme. Joseph Perraud×unknown seedling.

*Pollen parent.*—Unknown seedling.

Classification: Botanic and commercial—hybrid tea.

*Flower*

Blooming habit: (Observations made in the morning of June 29, 1940, at Newark, New York.) *Recurrent—continuous.*

Bud:

*Size.*—Large.

*Form.*—Pointed. Is not affected by wet or hot weather.

*Color.*—When sepals first divide—Scarlet, Plate I. When petals begin to unfurl—between Peach Red, Plate I, and Rose Doree, Plate I. When half blown: inside of petals—Rose Doree, Plate I; reverse of petals—Peach Red, Plate I.

*Sepals.*—Serrated, branched, "hood" above bud. Curl back when petals unfold. *Color:* outside—Absinthe Green, Plate XXXI; inside—Glass Green, Plate XXXI, with outer edge Yew Garden, Plate XXXI.

*Calyx.*—*Shape*—funnel. *Size*—small. *Aspect*—smooth. *Color*—Cress Green, Plate XXXI.

*Peduncle.*—*Length*—long. *Aspect*—rough. *Color*—Kronberg's Green, Plate XXXI. *Strength*—slightly bending.

*Opening.*—Bud opens well. Is not affected by adverse conditions.

Bloom:

*Size.*—Large. Average size when fully expanded—5 inches.

*Borne.*—Several together.

*Stems.*—Long; normal.

*Form.*—When first open, high center. *Permanence*—retains its form to the end.

*Petalage.*—Double (full but open center). Number of petals under normal conditions—22.

*Color.*—Center of flower—Rose Doree, Plate I. Outer petals—Geranium Pink, Plate I. Base of petals (aiglet)—Lemon Chrome, Plate IV. Inside of petals—Begonia Rose, Plate I, suffused with Lemon Chrome, Plate IV. Reverse of petals—Eosine Pink, Plate I, with Lemon Chrome, Plate IV. General tonality from a distance—Rose Doree, Plate I.

*Discoloration.*—General tonality at end of first day—Rose Doree, Plate I. Second day—Geranium Pink, Plate I. Third day—Eosine Pink, Plate I.

Petals:

*Texture.*—Thick. Is not affected by wet or hot weather.

*Appearance.*—Inside—satiny. Outside—shiny.

*Form.*—Oval.

*Arrangement.*—Informal (with "rags" in center). Petaloids in center—few; large.

*Persistence.*—Drop off cleanly.

*Fragrance.*—Slight. Nature—wild rose.

*Lasting quality.*—On the plant and as cut flower—long.

Genital organs:

*Stamens, Anthers.*—*Size*—medium; many. *Color*—Capucine Yellow, Plate III. *Arrangement*—regular around styles.

*Stamens, filaments (threads).*—Long. *Color*—Cadmium Yellow, Plate III.

*Pollen.*—Deep Chrome, Plate III.

*Styles.*—Bunched, uneven length; short; thin.

*Stigmas.*—Light Orange Yellow, Plate III.

*Ovaries.*—Most protruding from calyx, and some in calyx.

*Plant*

Form: Bush.

Growth: Vigorous, branching.

Foliage: 5–7 leaflets.

*Size.*—Medium.

*Quantity.*—Normal.

*Color.*—New foliage: upper side—Madder Brown, Plate XIII; under side—Van Dyke Red, Plate XIII.

Old foliage: upper side—Dark Cress Green, Plate XXXI; under side—Light Cress Green, Plate XXXI.

*Shape.*—Oval pointed.

*Texture.*—Upper side—glossy; under side—smooth. *Ribs and veins*—ordinary.

*Edge.*—Serrated.

*Serration.*—Double, small.

*Rachis.—Color*—Cress Green, Plate XXXI, under side—hooks.
*Stipules.*—Medium length; smooth.
*Disease resistance.*—Resistant.

Wood:
*New wood.—Color*—Pompeian Red, Plate XIII. *Bark*—rough.
*Old wood.—Color*—Cress Green, Plate XIII. *Bark*—smooth.

Thorns: (thorns are divided into thorns, prickles, and short needles):
*Thorns.—Quantity*—on main stalks from base and on laterals from stalk—many. *Form*—broad base; medium length, hooked downward. *Color when young*—Acajou Red, Plate XIII. *Position*—irregular.
*Prickles.—Quantity*—on laterals—few. *Color*—Eugenia Red, Plate XIII.

I claim:

A new and distinct variety of hybrid tea rose plant, characterized as to novelty by its vigorous branching habit, freedom of flowering, peculiar formation of the sepals, size of the calyx, number and arrangement of the ovaries, and the color of the flower, substantially as shown and described.

JEAN GAUJARD.